US010299848B2

United States Patent
Sara et al.

(10) Patent No.: US 10,299,848 B2
(45) Date of Patent: *May 28, 2019

(54) MULTI-LOBE BALLOON FOR CRYOABLATION

(71) Applicant: Medtronic CryoCath LP, Toronto (CA)

(72) Inventors: Rahmani Sara, Montreal (CA); Lies Safar Remali, Pointe-Claire (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/988,431

(22) Filed: May 24, 2018

(65) Prior Publication Data
US 2018/0263679 A1 Sep. 20, 2018

Related U.S. Application Data

(63) Continuation of application No. 14/944,870, filed on Nov. 18, 2015, now Pat. No. 10,058,371.

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00561* (2013.01); *A61B 2017/00955* (2013.01);
(Continued)

(58) Field of Classification Search
CPC ............ A61B 18/02; A61B 2018/0022; A61B 2018/00577; A61B 2018/00714;
(Continued)

(56) References Cited

U.S. PATENT DOCUMENTS 5,395,333 A 3/1995 Brill
6,338,727 B1 * 1/2002 Noda ................. A61F 7/12
604/113
(Continued)

OTHER PUBLICATIONS

Yun-Hyeon Kim, MD et al., Pulmonary Vein Diameter, Cross-sectional Area, and Shape: CT Analysis1, Published online before print, 10.1148/radiol.2351032106, Radiology 2005; 235: pp. 43-50.
(Continued)

*Primary Examiner* — Michael F Peffley
*Assistant Examiner* — Khadijeh A Vahdat
(74) *Attorney, Agent, or Firm* — Christopher & Weisberg, P.A.

(57) ABSTRACT

A cryotreatment catheter for treating tissue. The catheter may include an outer elongate body, a balloon treatment element coupled to the distal portion of the elongate body with a plurality of balloon lobes radially arranged around the outer elongate body, an inner elongate body rotatably movable within the lumen of the outer elongate body, and a fluid delivery lumen located within the lumen of the outer elongate body and at least partially within the lumen of the inner elongate body. The fluid delivery lumen may be branched at a distal portion into a plurality of linear segments, each linear segment being in fluid communication with one of the plurality of balloon lobes. Each of the balloon lobes may be inflated independently of each other by the linear segments of the fluid delivery lumen.

18 Claims, 12 Drawing Sheets

(52) U.S. Cl.
CPC ............... *A61B 2018/0022* (2013.01); *A61B 2018/00577* (2013.01); *A61B 2018/00714* (2013.01); *A61B 2018/00797* (2013.01); *A61B 2018/00863* (2013.01); *A61B 2018/00875* (2013.01); *A61B 2018/0212* (2013.01); *A61B 2018/0262* (2013.01)

(58) Field of Classification Search
CPC .......... A61B 2018/00797; A61B 2018/00875; A61B 2018/0212; A61B 2018/0262; A61B 2017/00561; A61B 2017/00955
USPC .................................................... 606/21–26
See application file for complete search history.

(56) References Cited

U.S. PATENT DOCUMENTS

| | | | |
|---|---|---|---|
| 6,496,737 B2 | 12/2002 | Rudie et al. | |
| 7,217,282 B2* | 5/2007 | Ginsburg | A61F 7/12 607/104 |
| 8,535,597 B2 | 9/2013 | Chen et al. | |
| 2008/0312644 A1* | 12/2008 | Fourkas | A61B 18/02 606/22 |
| 2010/0130970 A1* | 5/2010 | Williams | A61B 18/02 606/21 |
| 2012/0089047 A1 | 4/2012 | Ryba et al. | |

OTHER PUBLICATIONS

Abdulaziz Harbi et al., Anatomical variation of pulmonary venous ostium and its relationship with atrial arrhythmia in the Saudi population, Saudi Heart Assoc. Apr. 2014; 26(2): 81-85. Published online Dec. 16, 2013.

International Search Report and Written Opinion dated Jan. 19, 2017, for corresponding International Application No. PCT/CA2016/051295; International Filing Date: Nov. 8, 2016 consisting of 10 pages.

* cited by examiner

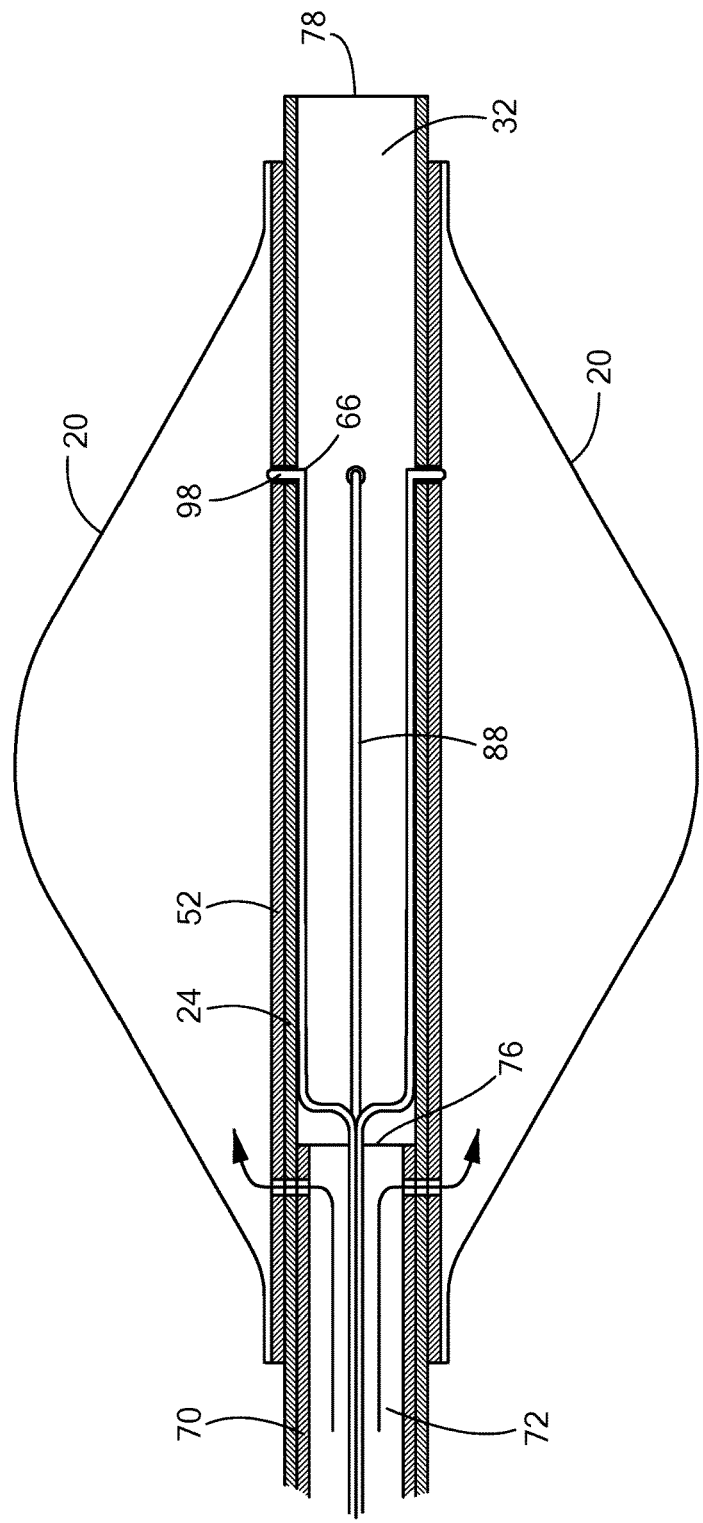

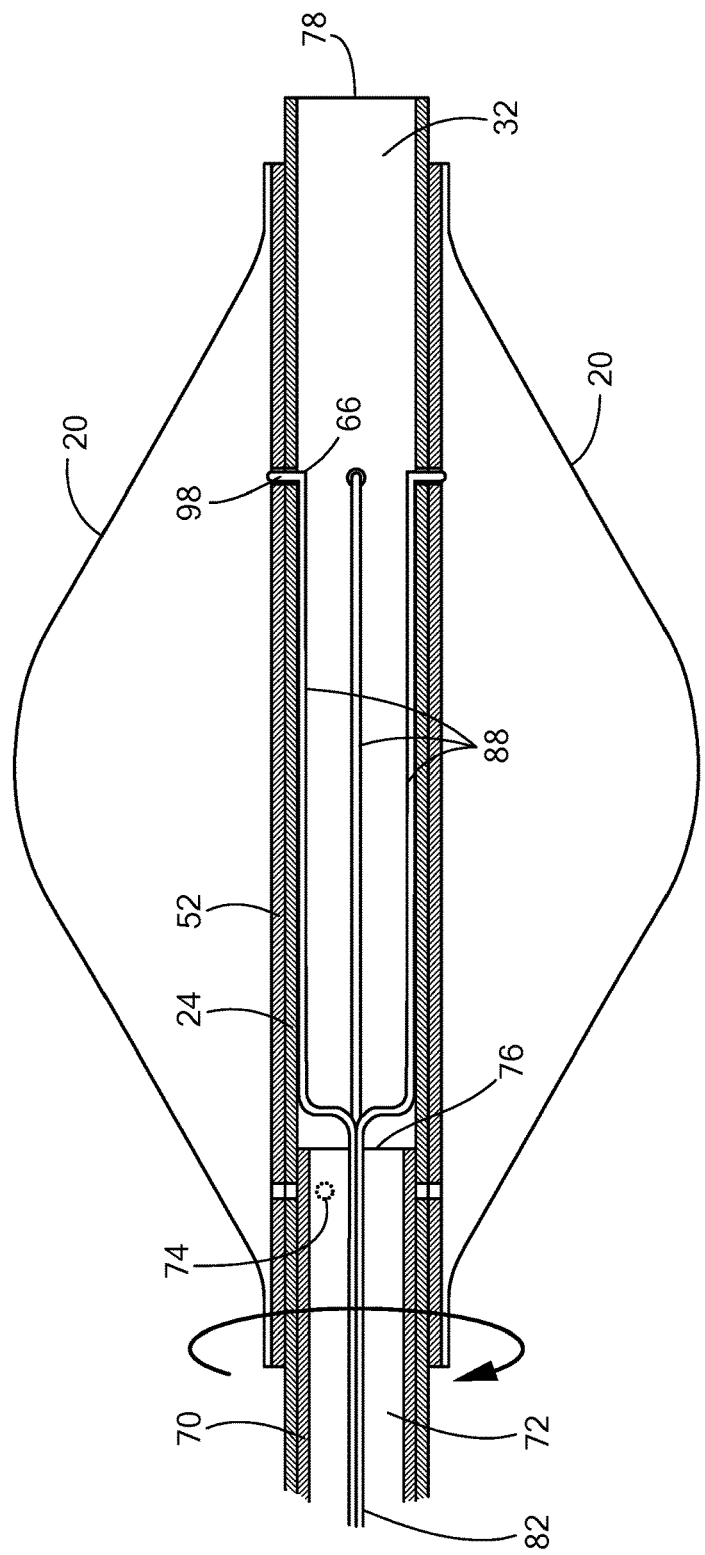

MULTI-LOBE BALLOON FOR CRYOABLATION

CROSS-REFERENCE TO RELATED APPLICATION

This application is a continuation of and claims priority to patent application Ser. No. 14/944,870, filed Nov. 18, 2015, Now U.S. Pat. No. 10,058,371, entitled MULTI-LOBE BALLOON FOR CRYOABLATION, the entirety of which is incorporated herein by reference.

STATEMENT REGARDING FEDERALLY SPONSORED RESEARCH OR DEVELOPMENT n/a

TECHNICAL FIELD

The present invention relates to an adjustable treatment device for accommodating a variety of pulmonary vein morphologies and a method of ablating tissue using the same.

BACKGROUND

A cardiac arrhythmia is a condition in which the heart's normal rhythm is disrupted. Certain types of cardiac arrhythmias, such as paroxysmal atrial fibrillation, may originate from an arrhythmogenic focus in or close to the pulmonary veins. Recent studies of pulmonary vein (PV) morphology showed that there is a wide variability in, for example, PV diameters at the ostia between the position of the veins within the same patient's heart (right superior PV, left superior PV, right inferior PV, and left inferior PV). These studies also showed that the diameter and cross-sectional area of the left superior PV are gender dependent, being significantly larger in men than in women.

Many types of cardiac arrhythmia may be treated by various ablation methods, including cryoablation. Data analysis of cryotherapy procedures showed that the use of cryoballoon catheters in combination with focal or radiofrequency (RF) catheters is common. Generally speaking, the focal or RF catheters are used to access sections of the PVs at the ostia that are inaccessible using only the cryoballoon catheter or that still exhibit conduction of aberrant electrical signals after cryoballoon ablation. The average rate of using such touch-up methods for three consecutive years was about 11% (2011, 2012, and 2013).

Given the variation in PV morphology between patients of different genders and, indeed, within a single patient, means that treating arrhythmia using a one-size-fits-all cryoballoon catheter without the need for one or more touch-up procedures is nearly impossible. As the need for focal or RF catheter ablation following cryoablation poses a safety risk to the patient and increases procedure time, it is desirable to provide a cryoablation device that can be adjusted to accommodate a variety of PV morphologies, such as PV diameter, cross-sectional area, shape, etc.

SUMMARY

The present invention advantageously provides a device and system that is adjustable for accommodating a variety of pulmonary vein morphologies and a method of ablating tissue using the same. A cryotreatment catheter may generally include an elongate body including a distal portion, a proximal portion, and lumen therebetween, and a balloon treatment element coupled to the distal portion of the elongate body, the balloon treatment element including a plurality of balloon lobes radially arranged around the elongate body. For example, the balloon treatment element may include at least six balloon lobes. The distal portion of the elongate body may include a first plurality of apertures and a second plurality of apertures located distal to the first plurality of apertures, each of the first and second pluralities of apertures being radially arranged around the elongate body and corresponding to one of the plurality of balloon lobes. Each of the plurality of balloon lobes may include a first aperture that is radially aligned with one of the plurality of first apertures of the elongate body, and a second aperture that is radially aligned with one of the plurality of second apertures of the elongate body, the second aperture being located distal to the first aperture. The elongate body may be an outer elongate body, and the cryotreatment catheter may further include an inner elongate body including a distal portion, a proximal portion, a lumen therebetween, and a plurality of apertures radially arranged around the inner elongate body. Each of the plurality of apertures of the inner elongate body may correspond to one of the first plurality of apertures of the outer elongate body. Further, the distal portion of the inner elongate body may define a distal end, the distal end of the inner elongate body being distal to the first plurality of apertures of the outer elongate body. The cryotreatment catheter further may include a delivery lumen at least partially located within the inner elongate body. The delivery lumen may include a proximal portion located within the inner elongate body, and a branched distal portion located within the outer elongate body distal to the distal end of the inner elongate body, the branched distal portion including a plurality of linear segments, each of the plurality of linear segments being in fluid communication with a corresponding one of the plurality of balloon lobes. Each of the linear segments may include a distal tip portion that has a delivery aperture, each of the distal tip portions extending from a corresponding linear segment at an approximately 90° angle, each of the distal tip portions extending through a corresponding one of the second plurality of apertures of the outer elongate body and a corresponding second aperture of one of the plurality of balloon lobes. The lumen of the outer elongate body may be configured to be in fluid communication with a vacuum source and a fluid reservoir.

A cryotreatment catheter may include: an outer elongate body including a distal portion, a proximal portion, and a lumen extending between the distal portion and the proximal portion, the distal portion defining a distal end; a balloon treatment element coupled to the distal portion of the elongate body, the balloon treatment element including a plurality of balloon lobes radially arranged around the outer elongate body; an inner elongate body located within and rotatably and/or linearly movable within the lumen of the outer elongate body, the inner elongate body including a distal portion, a proximal portion, and a lumen extending between the distal portion and the proximal portion, the distal portion defining a distal end that is located proximal to the distal end of the outer elongate body; a fluid delivery lumen located within the lumen of the outer elongate body and at least partially within the lumen of the inner elongate body. The outer elongate body may include a first plurality of apertures and a second plurality of apertures located distal to the first plurality of apertures, each of the first and second pluralities of apertures being radially arranged around the elongate body and corresponding to one of the plurality of balloon lobes. each of the plurality of balloon lobes may include a first aperture that is radially aligned with one of the plurality of first apertures of the elongate body, and a second aperture that is radially aligned with one of the plurality of second apertures of the elongate body, the second aperture being located distal to the first aperture. The inner elongate body may include a plurality of apertures radially arranged around the inner elongate body, each of the apertures of the inner elongate body corresponding to one of the first plurality of apertures of the outer elongate body. The plurality of balloon lobes may include at least six balloon lobes. The fluid delivery lumen may include: a proximal portion located within the inner elongate body; a branched distal portion located within the outer elongate body, the branched distal portion including a plurality of linear segments, each of the plurality of linear segments being in fluid communication with a corresponding one of the plurality of balloon lobes; and a divergence point between the proximal portion and the branched distal portion, the divergence point being distal to the distal end of the inner elongate body. Each of the linear segments may include a distal tip portion that has a delivery aperture, each of the distal tip portions extending from a corresponding linear segment at an approximately 90° angle, each of the distal tip portions extending through a corresponding one of the second plurality of apertures of the outer elongate body and a corresponding second aperture of one of the plurality of balloon lobes. Each of the outer elongate body and the inner elongate body may include a longitudinal axis, the longitudinal axis of the inner elongate body being coaxial with the longitudinal axis of the outer elongate body, and the inner elongate body is configured to obstruct the first plurality of apertures of the outer elongate body when the inner elongate body is rotated and/or linearly moved along its longitudinal axis.

A cryotreatment catheter may include: an outer elongate body including a longitudinal axis, a distal portion, a proximal portion, and a lumen extending between the distal portion and the proximal portion, the distal portion defining a distal end, the outer elongate body further including a first plurality of apertures and a second plurality of apertures located distal to the first plurality of apertures; a balloon treatment element coupled to the distal portion of the elongate body, the balloon treatment element including a plurality of balloon lobes radially arranged around the outer elongate body, each of the plurality of balloon lobes having an attachment spine and a tissue contact surface, a first plurality of apertures, and a second plurality of apertures located distal to the first plurality of apertures, the first plurality of apertures of the balloon lobes being radially aligned with the first plurality of apertures of the outer elongate body and the second plurality of apertures of the balloon lobes being radially aligned with the second plurality of apertures of the outer elongate body; an inner elongate body located within and rotatably movable within the lumen of the outer elongate body, the inner elongate body including a longitudinal axis that is coaxial with the longitudinal axis of the outer elongate body, a distal portion, a proximal portion, a lumen extending between the distal portion and the proximal portion, and a plurality of apertures at the distal portion, the distal portion defining a distal end that is located proximal to the distal end of the outer elongate body, and the plurality of apertures of the inner elongate body being configured to be radially aligned with the first plurality of apertures of the outer elongate body and the first plurality of apertures of the balloon lobes, the inner elongate body being configured to obstruct the first plurality of apertures of the outer elongate body when the inner elongate body is rotated along its longitudinal axis; and a fluid delivery lumen including a proximal portion, a branched distal portion, and a divergence point therebetween, the divergence point being located distal to the plurality of apertures of the inner elongate body.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 9A-9D show configurations of an inner elongate body within a treatment catheter during a cryotreatment procedure.

DETAILED DESCRIPTION

Figure 1:
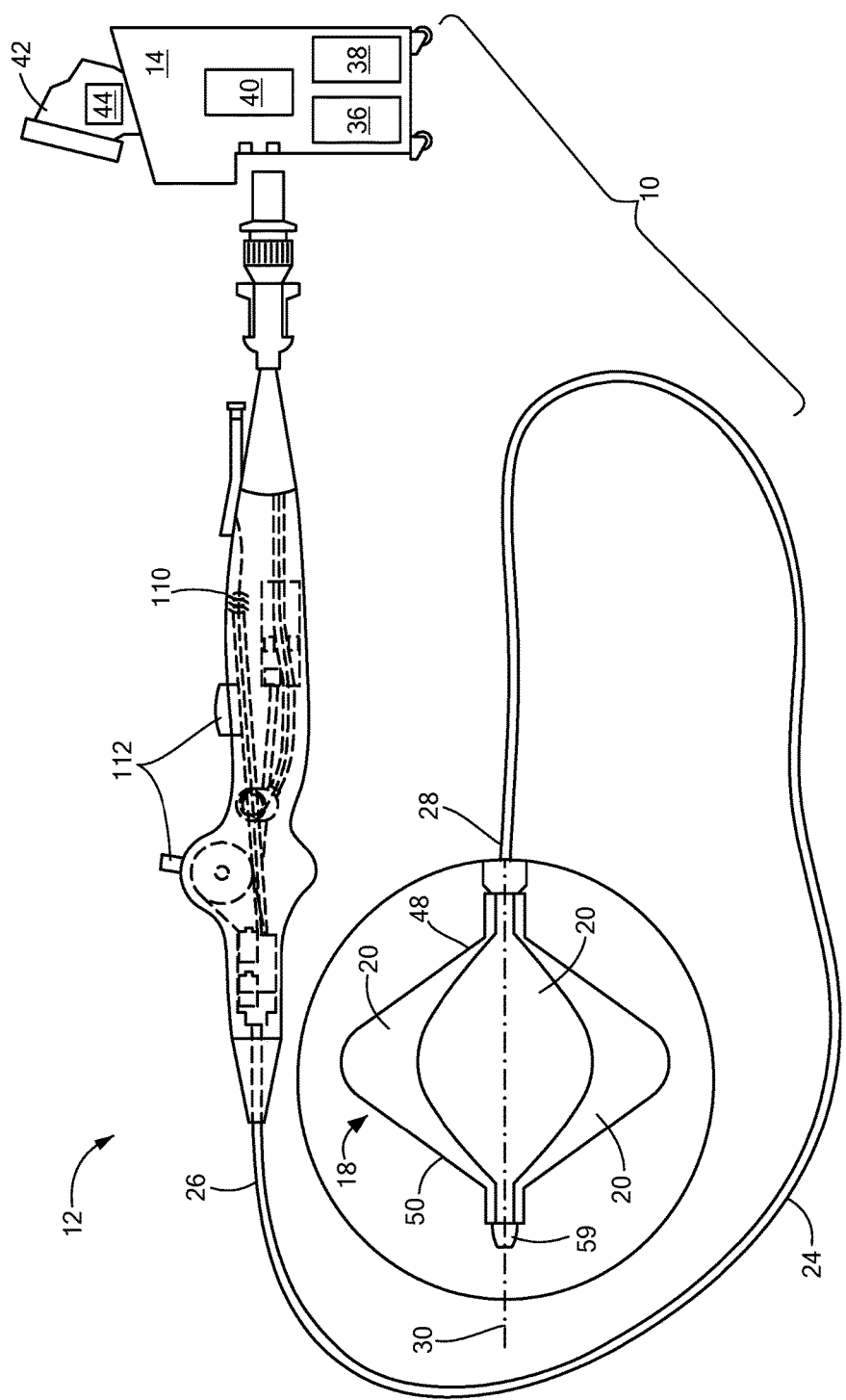
FIG. 1 shows an exemplary system including a treatment catheter having an adjustable balloon treatment element.

The present invention advantageously provides a device and system that is adjustable for accommodating a variety of pulmonary vein morphologies and a method of ablating tissue using the same. Referring now to the drawing figures in which like reference designations refer to like elements, an exemplary system including a cryoablation catheter having an adjustable cryoballoon treatment element is shown in FIG. 1 and generally designated as "10." The device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

The system 10 may generally include a treatment catheter 12 and a control unit 14 in communication with the treatment device 12. The treatment device 12 may be, for example, a cryoballoon catheter and the control unit 14 may be configured for use with a cryotreatment procedure. The cryotreatment catheter 12 may include a balloon treatment element 18 that includes a plurality of balloon lobes 20. As is described in more detail below, each of the balloon lobes 20 may be inflated and deflated independently of each other.

Referring to the treatment catheter 12 in more detail, the catheter 12 may include an elongate body 24 passable through a patient's vasculature and/or positionable proximate to a tissue region for diagnosis or treatment, such as a catheter, sheath, or intravascular introducer. The elongate body 24 may include a proximal portion 26, a distal portion 28, and a longitudinal axis 30, and may further include one or more lumens disposed within the elongate body 24 that provides mechanical, electrical, and/or fluid communication between the elongate body proximal portion 26 and the elongate body distal portion 28. For example, the elongate body 24 may include a main lumen 32. The balloon treatment element 18 may be coupled to the distal portion 28 of the elongate body 24, with the plurality of balloon lobes 20 being radially arranged about the elongate body 24.

Continuing to refer to FIG. 1, the control unit 14 may include a fluid supply including one or more reservoirs 36 for one or more coolants, cryogenic refrigerants, or the like, an exhaust or scavenging system for recovering or venting expended fluid for reuse or disposal (including, for example, a recovery reservoir and vacuum pump), as well as various control mechanisms. The control unit 14 may also include an additional fluid supply including a reservoir 38 containing a non-coolant liquid, gas, or combination liquid and gas used to inflate the balloon lobes 20, which fluid may be referred to as "inflation fluid." In addition to providing an exhaust function for the inflation fluid and/or refrigerant reservoirs, the control unit 14 may also include pumps, valves, controllers or the like to recover and/or re-circulate fluid delivered to various fluid pathways of the catheter. A vacuum pump 40 in the control unit 14 may create a low-pressure environment in one or more conduits within the catheter so that fluid is drawn into the conduits/lumens of the elongate body 24, away from the distal portion 28 and toward the proximal portion 26 of the elongate body 24.

The control unit 14 may also include one or more components for the manual, automatic, and/or semi-automatic regulation of the system, such as a computer 42 having one or more processors 44 for executing one or more algorithms for the automatic or semi-automatic regulation of the catheter 12 before, during, and after an ablation procedure. For example, the one or more processors 44 may be programmable to at least partially inflate and at least partially deflate the plurality of balloon lobes 20, to regulate temperature of the balloon treatment element 18, and/or to receive and interpret mapping or sensor signals from the cryotreatment catheter 12 or another device used as part of a medical procedure. The control unit 14 may also include, for example, a proportional valve that regulates inflation of the balloon treatment element 18 during the transition between the inflation phase and the ablation phase. Although various system components may be shown and described herein as being within the control unit 14, the term "control unit" as used herein refers to any system component other than the cryotreatment catheter and other devices that are passed into the patient to perform the medical procedure, regardless of whether the components are physically located within the control unit 14.

Figure 2:
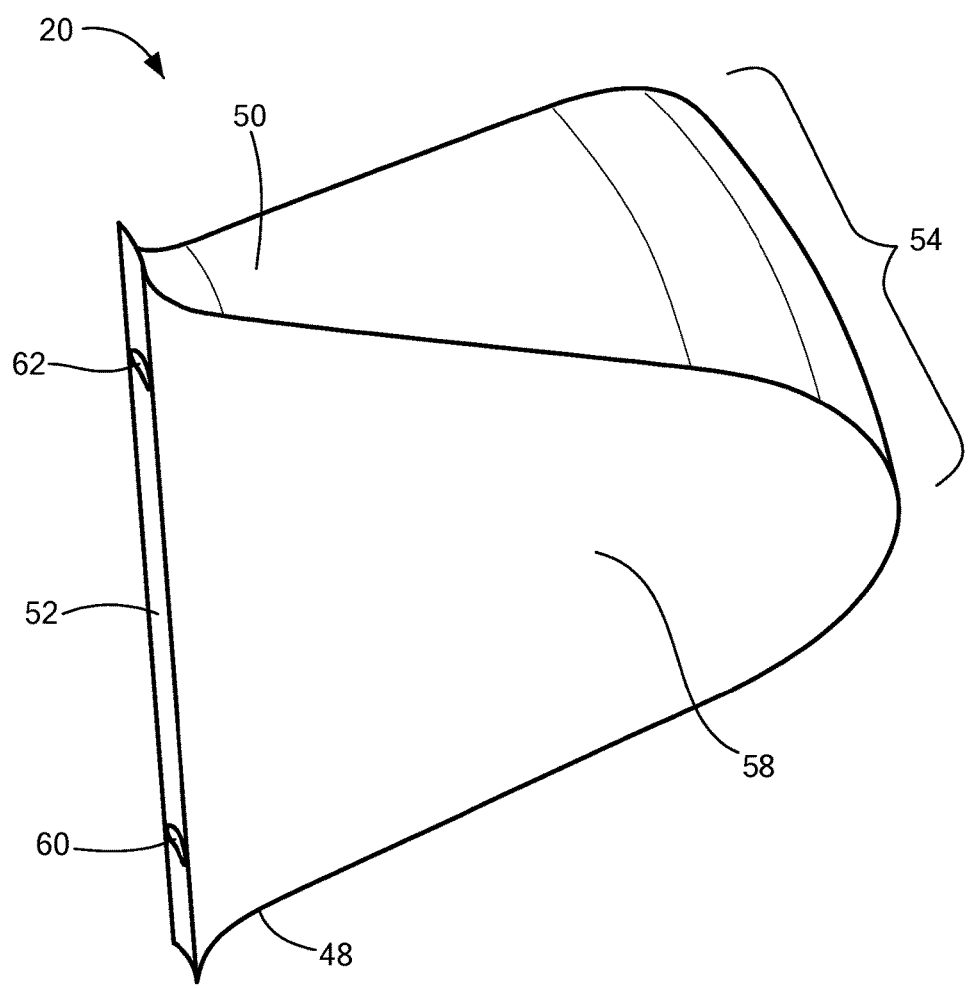
FIG. 2 shows a balloon lobe.

Referring now to FIG. 2, the balloon treatment element 18 may be, for example, a cryotreatment element. As shown in the figures, the balloon treatment element 18 may include a plurality of balloon lobes 20 radially arranged about the elongate body 24. As a non-limiting example, the balloon treatment element 18 may include six balloon lobes, although fewer or more balloon lobes 20 may be included. Each of the balloon lobes 20 may include a proximal portion 48, a distal portion 50, and an attachment spine 52 proximate the elongate body 24, a tissue contact surface 54 opposite the attachment spine 52, and each lobe 20 may define an inner chamber 56. Further, each balloon lobe 20 may include two lateral surfaces 58 that are in contact with the lateral surfaces 58 of adjacent lobes 20. Each balloon lobe 20 may be shaped approximately like a section of an orange and the attachment spine 52 of each lobe 20 may be affixed to the distal portion 28 of the elongate body 24. As a non-limiting example, each attachment spine 52 may be affixed proximally to the elongate body distal portion 28 and distally to a distal tip 59 using an adhesive, chemical or thermal bonding, or other suitable attachment means (for example, as shown in FIG. 1). Alternatively, each attachment spine 52 may be affixed proximally and distally to the elongate body 24 (for example, as shown in FIGS. 3A and 9A-9D). Further, each attachment spine 52 may include a first (proximal) aperture 60 and a second (distal) aperture 62. Likewise, the distal portion 28 of the elongate body 24 may include a plurality of first (proximal) apertures 64, each of which corresponding to an adjacent first aperture 60 of a balloon lobe attachment spine 52. For example, if the balloon treatment element 18 includes six balloon lobes 20 each having a first aperture 60, the distal portion 28 of the elongate body 24 may include six first apertures 64 that are radially arranged about the elongate body 24 longitudinal axis and configured to match up with or be in fluid communication with each of the balloon lobe first apertures 60. The distal portion 28 of the elongate body 24 may further include a plurality of second (distal) apertures 66, each of which corresponding to an adjacent second aperture 62 of a balloon lobe attachment spine 52. For example, if the balloon treatment element 18 includes six balloon lobes 20 each having a second aperture 62, the distal portion 28 of the elongate body 24 may include six second apertures 66 that are radially arranged about the elongate body 24 longitudinal axis 30 and configured to match up with or be in fluid communication with each of the balloon lobe second apertures 62. Each of the apertures disclosed herein may be a round or substantially round hole in the wall of the elongate body 24 or the balloon lobe attachment spine 52. However, it will be understood that the apertures may be of any size or configuration that allows the passage of fluid therethrough. Further, the diameter of each aperture may be sized to provide a desired fluid flow rate.

Figure 3:
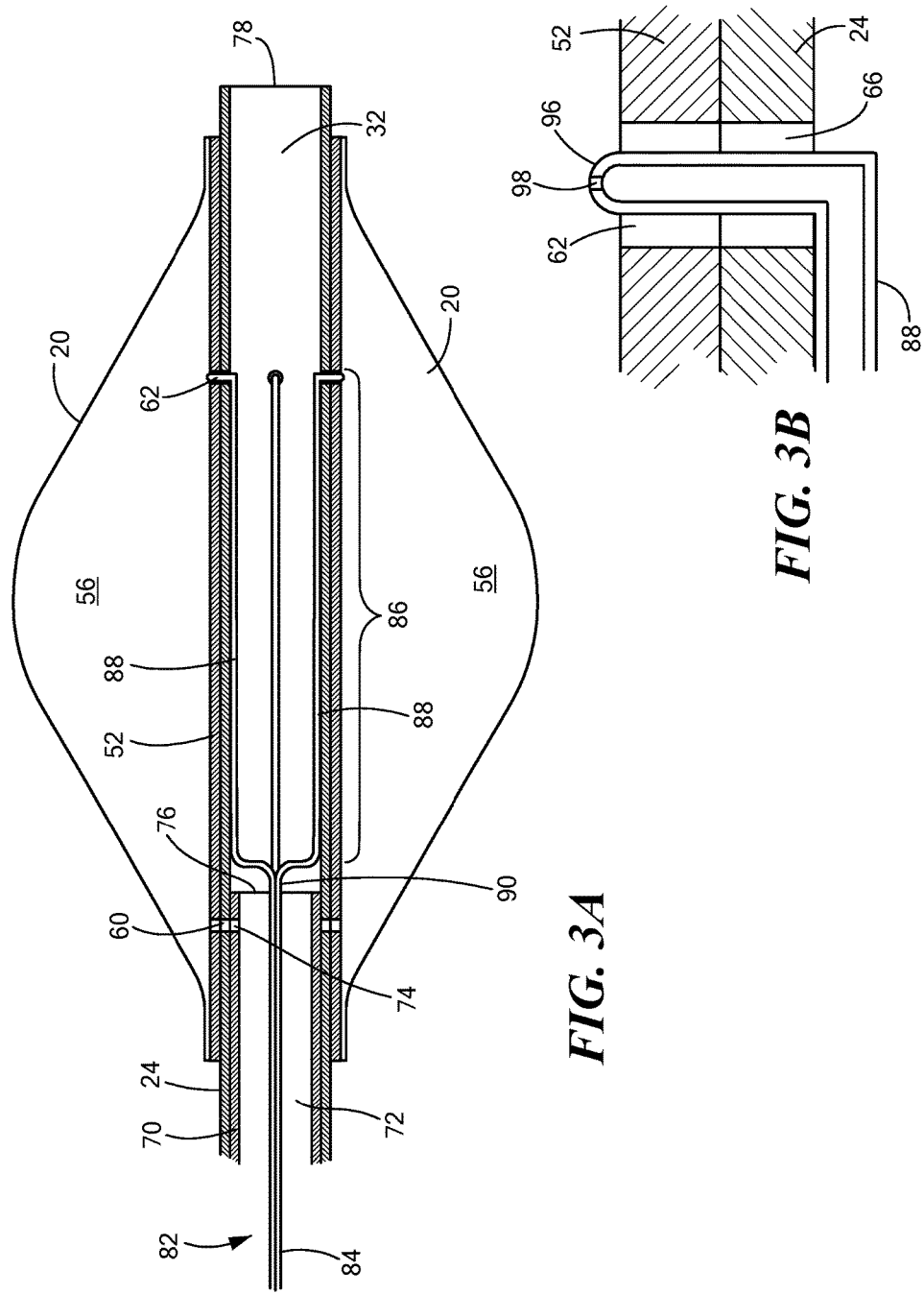
FIG. 3A shows a cross-sectional view of a fluid delivery lumen within the treatment catheter of FIG. 1.
FIG. 3B shows a close-up view of a portion of the fluid delivery lumen.

Referring now to FIGS. 3A and 3B, the elongate body 24 may define a main lumen 32, which may function as both an inflation lumen and an exhaust lumen. The catheter 12 may also include an inner elongate body 70 defining an inner lumen 72, and the inner elongate body 70 may be rotatable and/or longitudinally (linearly) movable within the main lumen 32 of the elongate body 24, which may be referred to as being an outer elongate body 24 relative to the inner elongate body 70. The inner elongate body 70 may also include a plurality of apertures 74 that may be radially and longitudinally aligned with the first apertures 64 of the elongate body 24 and the first apertures 60 of the balloon lobes 20, such that rotation and/or longitudinal movement of the inner elongate body 70 in at least one direction may selectively obscure/obstruct or unobscure/unobstruct the first apertures 64 of the elongate body 24 and the first aperture 60 of each of the balloon lobes 20. Additionally or alternatively, the inner elongate body 70 may be advanced or retracted within the main lumen 32 to selectively obscure/obstruct or unobscure/unobstruct the first apertures 64, 60 of the elongate body 24 and the balloon lobes 20. The elongate body 24 and the inner elongate body 70 may each define a proximal portion and a distal portion, with each distal portion defining a distal end. The distal end 76 of the inner elongate body 70 may be at a location that is proximal to the distal end 78 of the elongate body 24 (as shown in FIG. 3A).

The catheter 12 may also include a delivery lumen 82 that includes a proximal portion 84 and a distal portion 86. At least a portion of the proximal portion 84 of the delivery lumen 82 may be located within the inner elongate body lumen. The distal portion 86 of the delivery lumen 82 may be branched into a plurality of linear segments 88, with each linear segment 88 being in fluid communication with one of the plurality of balloon lobes 20 through the second apertures 66 of the elongate body 24 and the second aperture 62 of the balloon lobe 20. Further, the proximal portion 84 of the delivery lumen 82 may end, and the distal portion 86 of the delivery lumen 82 may begin, at a branch or divergence point 90 location that is distal to the distal end 76 of the inner elongate body 70 and distal to the elongate body first apertures 64 (as shown in FIG. 3A).

As is shown in detail in FIG. 3B, each linear segment 88 of the distal portion 86 of the delivery lumen 82 may include a distal tip portion that includes a fluid delivery segment 96. The fluid delivery segment 96 extend from the linear segment 88 at an approximately 90° angle (±) 5°, forming an L shape. Thus, each branch of the delivery lumen distal portion 86 may be referred to herein as being "L shaped." Each of the fluid delivery segments 96 may extend at least partially through a corresponding second aperture 66 of the elongate body 24 and a second aperture 62 of a balloon lobe 20 to be in fluid communication with the lobe inner chamber 56. The tip of the fluid delivery segment 96 may define or include a delivery aperture 98, through which an inflation and/or cryogenic fluid may be delivered to the inner chamber of the balloon lobe 20. The second apertures 66 of the elongate body 24 and the second apertures 62 of the balloon lobes 20 may be sized and configured such that they are able to receive the fluid delivery segment 96 of each linear segment but without allowing inflation fluid and/or cryogenic refrigerant to leak back into the main lumen 32. For example, the fluid delivery segment 96 may be friction fit and/or coupled within the second aperture 66 of the elongate body 24 and the second aperture 62 of the balloon lobes 20 (such as with an adhesive, chemical or thermal bonding, or other suitable means). A proximal portion of each linear segment 88 may pass through a sheath or lumen to form a bundle, or may be coupled to one another to form a bundle, and this bundle may be referred to as the proximal portion 84 of the delivery lumen 82.

Figure 4:
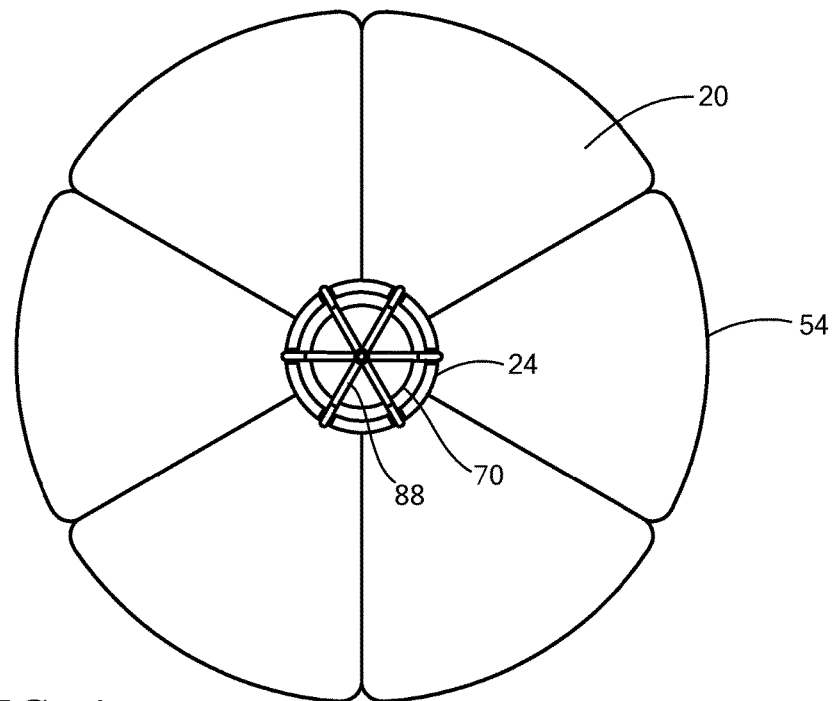
FIG. 4 shows a distal cross-sectional view of a first embodiment of the balloon treatment element with all lobes being fully inflated.
Figure 5:
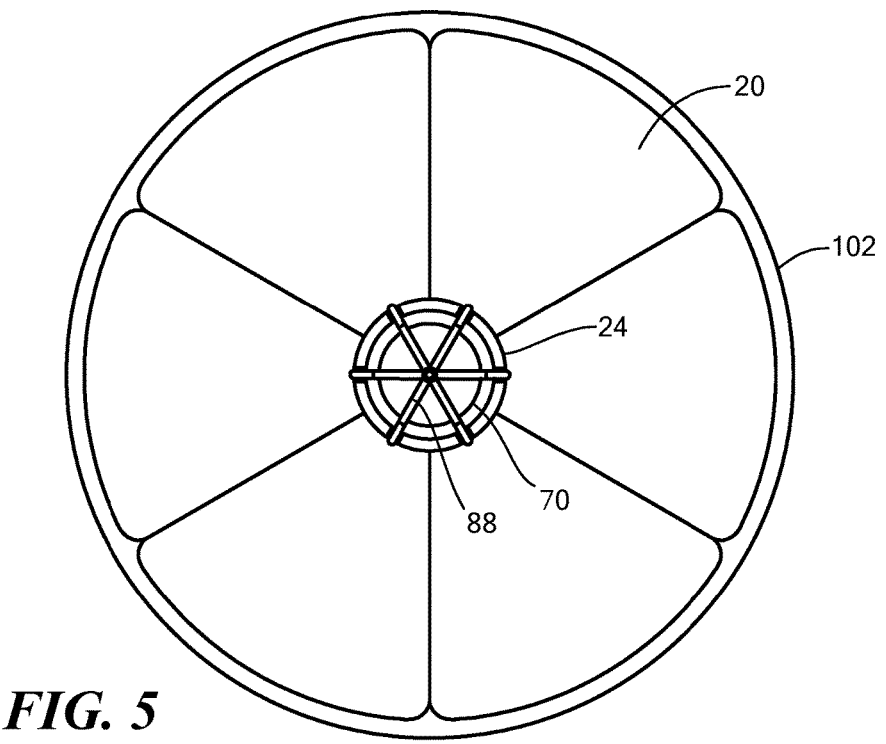
FIG. 5 shows a distal cross-sectional view of a second embodiment of the balloon treatment element with all lobes being fully inflated.

Referring now to FIGS. 4 and 5, distal cross-sectional views of two embodiments of the balloon treatment element are shown. In the first embodiment shown in FIG. 4, the balloon treatment element 18 may include only a plurality of balloon lobes 20. In the second embodiment shown in FIG. 5, however, the balloon treatment element 18 may also include an outer balloon 102 that surrounds the plurality of balloon lobes 20. The outer balloon 102 may be composed of a material that is more compliant than the material from which the plurality of balloon lobes 20 are composed, and the outer balloon 102 may help smooth the transitional curves between the balloon lobes 20 and create a smooth tissue contact surface that covers all or at least substantially all of the balloon treatment element 18. The outer balloon 102 may include a distal neck and a proximal neck (not shown) that are affixed or coupled to the distal tip 59 and the distal portion 28 of the elongate body 24, respectively. Alternatively, the outer balloon 102 may be coupled to the elongate body 24 in another suitable manner.

Although not shown, the treatment catheter 12 may also be configured for use with other energy modalities, such as radiofrequency energy, microwave energy, laser energy, ultrasound energy, electroporation energy, and the like. Therefore, it will be understood that the balloon treatment element 18 may also include one or more electrodes and/or other energy delivery elements. As a non-limiting example, the balloon treatment element 18 may include one or more fiber sensors located within the balloon lobes 20 and/or between the balloon lobes 20 and the outer balloon for temperature assessment of the ablated tissue and/or strain assessment. Further, the one or more fiber sensors may be used for hyperspectral assessment of the targeted tissue. The medical system may also include one or more sensors to monitor the operating parameters throughout the system, including for example, pressure, temperature, flow rates, volume, or the like in the control unit 14, and/or the catheter 12. For example, the catheter 12 may further include one or more temperature and/or pressure sensors (not shown) proximate and/or within the balloon treatment element 18 for monitoring, recording or otherwise conveying measurements of conditions within the medical device or the ambient environment at the distal portion of the medical device. The sensor(s) may be in communication with the control unit 14 for initiating or triggering one or more alerts or therapeutic delivery modifications during operation of the medical device.

The treatment catheter 12 may include a handle 110 coupled to the proximal portion 26 of the elongate body 24 and/or the inner elongate body 70. The handle 110 may include one or more actuation elements 112, such as sliders, levers, or knobs, for manipulating the elongate body 24, inner elongate body 70, and/or additional components of the medical device. For example, the handle 110 may include a knob that is in mechanical communication with the inner lumen, such that rotation of the knob may produce a similar rotation of the inner lumen within the main lumen 32 of the elongate body 24. Additionally or alternatively, rotation of the inner elongate body 70 may be controlled automatically or semi-automatically by the control unit 14. For example, the handle 110 may include a geared motor controlled by the control unit 14 to transmit movement to the elongate body 70. Alternatively or additionally, the handle 110 may include a slider, lever, or other actuation element that is also in mechanical communication with the inner elongate body 70 such that activation of the actuation element selectively advances or retracts (that is, longitudinally moves) the inner elongate body 70 in at least one longitudinal direction and/or rotates the inner elongate body 70 in a clockwise or counterclockwise direction. The handle 110 may further include circuitry for identification and/or use in controlling of the catheter or another component of the system 10. Additionally, the handle 110 may be provided with a fitting for receiving a guide wire that may be passed into the main lumen 32 or a guidewire lumen (not shown).

Figure 6A:
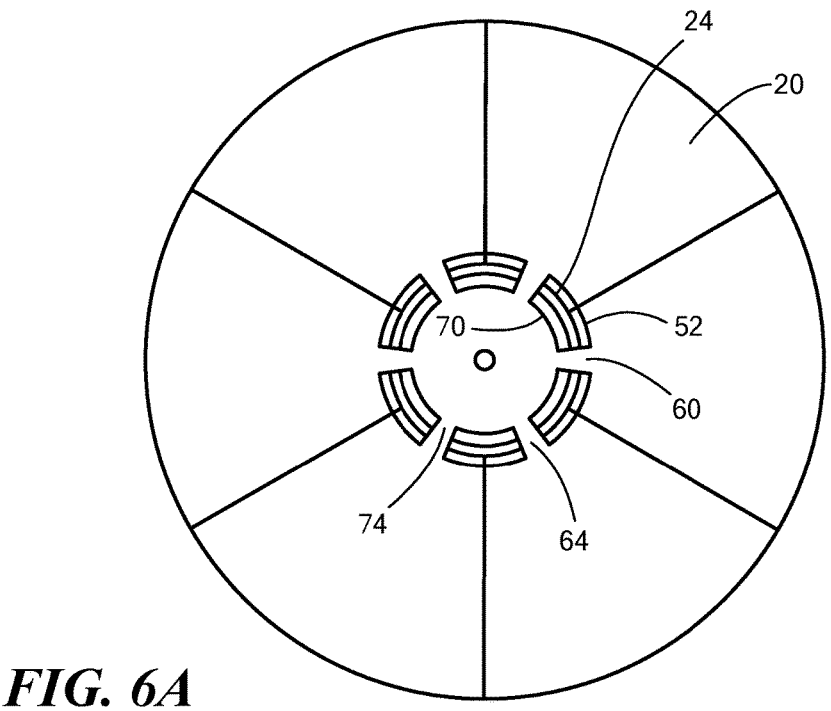
FIG. 6A shows a general inflation position of an inner lumen relative to the balloon treatment element.
Figure 6B:
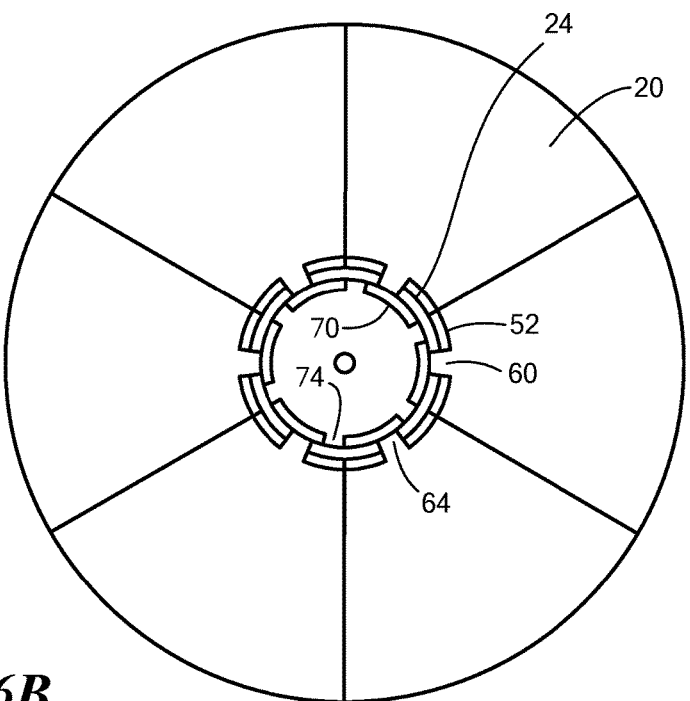
FIG. 6B shows a precision inflation position of the inner lumen relative to the balloon treatment element.
Figure 6C:
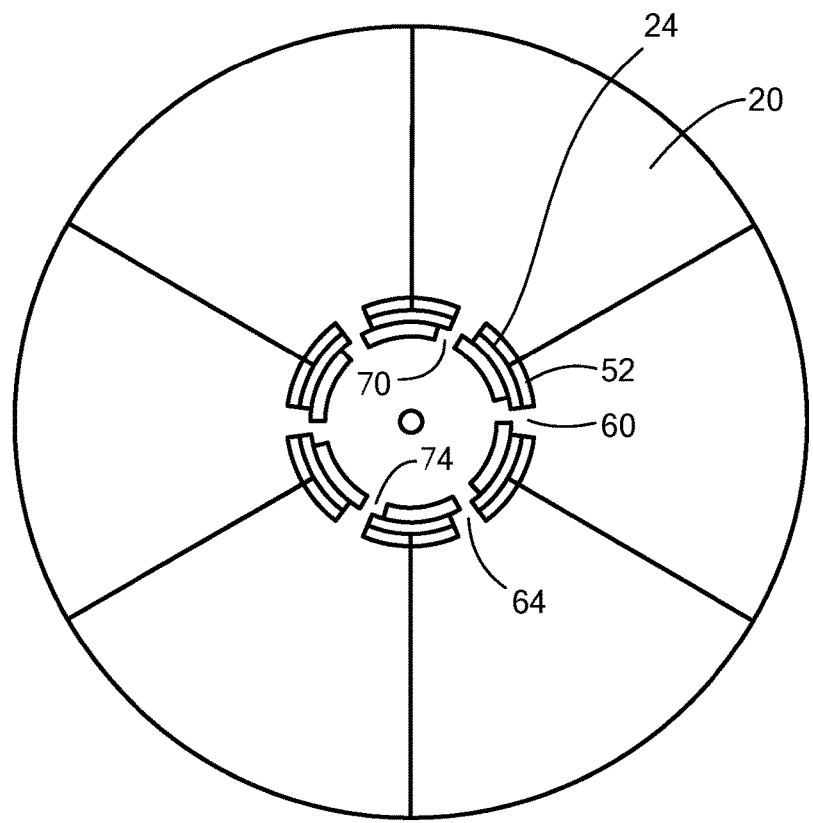
FIG. 6C shows an ablation position of the inner lumen relative to the balloon treatment element.

Referring now to FIGS. 6A-6C, various positions of the inner elongate body relative to the balloon treatment element are shown. For simplicity, the delivery lumen 82 and linear segments 88 are not shown as it is in FIGS. 4 and 5. As described above, the inner elongate body 70 may include a plurality of apertures 74, each of which corresponding to an elongate body first aperture 64 and a balloon lobe first aperture 60. For example, if the balloon treatment element 18 includes six lobes, the inner elongate body 70 may include six apertures. As shown in FIG. 6A, the balloon treatment element 18 may be inflated when the inner elongate body 70 is rotated such that the apertures 74 of the inner elongate body 70 are aligned with or correspond to the first apertures 64 of the elongate body 24 and the first apertures 60 of the balloon lobes 20. In this configuration, an inflation fluid may be delivered to the inner chambers 56 of the balloon lobes 20 through the main lumen 32 of the elongate body 24, through the apertures 74 of the inner elongate body 70, through the first apertures 64 of the elongate body 24, and through the first apertures 60 of the balloon lobes 20. As shown in FIG. 6B and described in more detail below, each balloon lobe 20 may be further selectively inflated when the inner elongate body 70 is rotated such that the inner elongate body 70 apertures 74 are not aligned with or correspond to the first apertures 60 of the balloon lobes 20 and the first apertures 64 of the elongate body 24. In this configuration, inflation fluid within the balloon lobes 20 is prevented from evacuating through the first apertures 60, 64 and further inflation fluid may be precisely delivered to one or more lobes 20 by one or more linear segments 88 of the delivery lumen 82. Finally, as shown in FIG. 6C, the inflation fluid may be evacuated and replaced by a cryogenic refrigerant as it flows without affecting the inflation level of each balloon lobe 20 when the inner elongate body 70 is rotated such that the inner elongate body apertures 74 are only partially aligned with or corresponding to the first apertures 60 of the balloon lobes 20 and the first apertures 64 of the elongate body 24. In this configuration, the flow rate and/or injection pressure of the cryogenic refrigerant being delivered by the delivery lumen 82 to each balloon lobe 20 may be balanced by the evacuation rate of the fluid from the balloon lobes 20 through the inner elongate body apertures 74.

Figure 7:
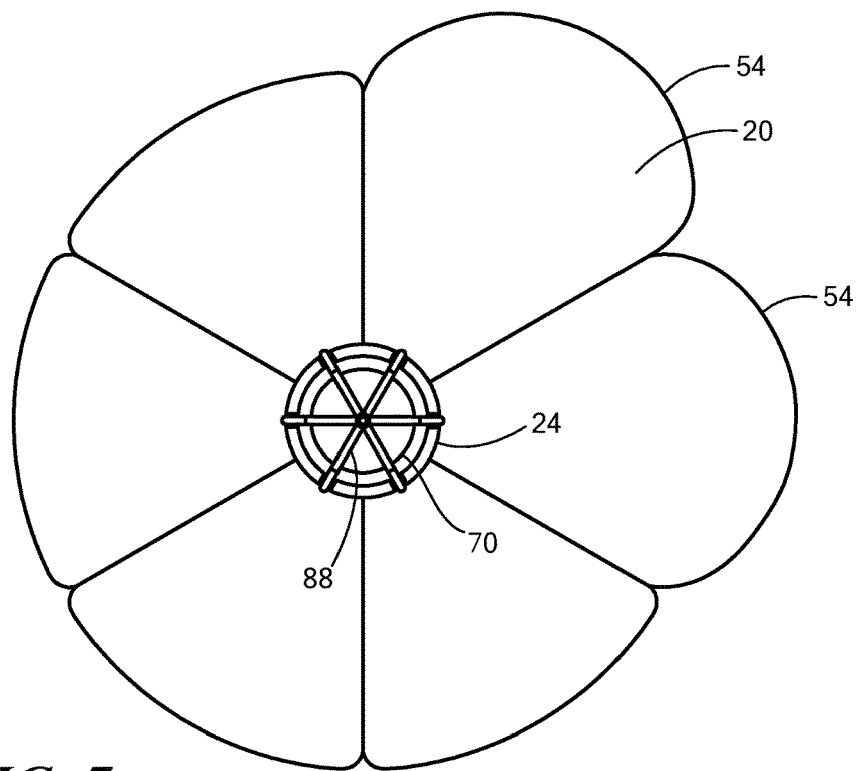
FIG. 7 shows a distal cross-sectional view of a first example of an asymmetrical inflation of the balloon treatment element.
Figure 8:
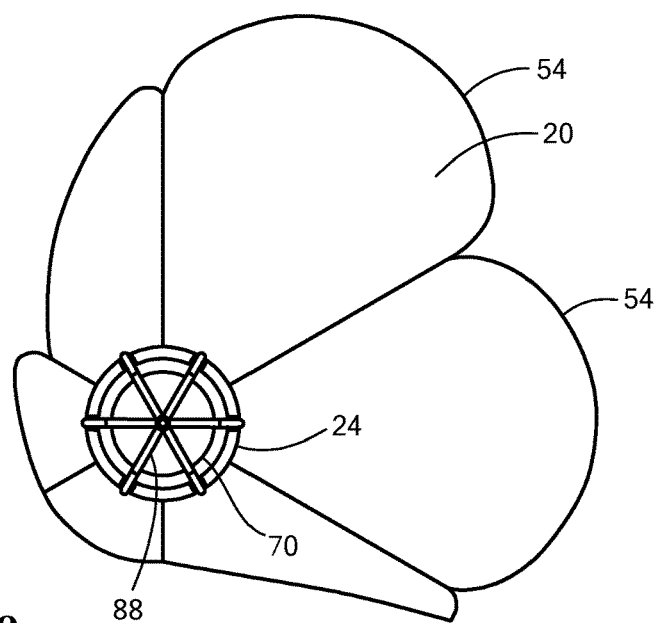
FIG. 8 shows a distal cross-sectional view of a second example of an asymmetrical inflation of the balloon treatment element.

Referring now to FIGS. 7 and 8, examples of asymmetrical inflation of the balloon treatment element are shown. As is described in more detail below, each balloon lobe 20 may be inflated independently of the others in order to ensure contact between the balloon treatment element 18 and a variety of target tissue configurations. As is shown in FIG. 7, for example, the balloon treatment element 18 may be initially inflated and positioned at a pulmonary vein ostium, or at least partially inserted into the pulmonary vein. Then, each balloon lobe 20 may be precisely inflated as needed, depending on the morphology of the pulmonary vein. This may be particularly useful when the pulmonary vein has a non-circular or irregular cross section on which it is difficult to produce a circumferential lesion with traditional, non-lobed cryoballoons. Likewise, the balloon treatment element 18 may be inflated to contact a lateral area of target tissue. As shown in FIG. 8, for example, the balloon treatment element 18 may be initially inflated and positioned proximate an area of target tissue on a cardiac wall. Then, the balloon lobes that are not in contact with the target tissue may not be inflated at all and the balloon lobes that are in contact with the target tissue may be inflated using the delivery lumen 82 and the linear segments corresponding to each of the balloon lobes to be inflated. Deflating or not inflating the balloon lobes that are not in contact with the target tissue may reduce the warming effect of surrounding blood on the balloon treatment element 18.

Figure 9C:
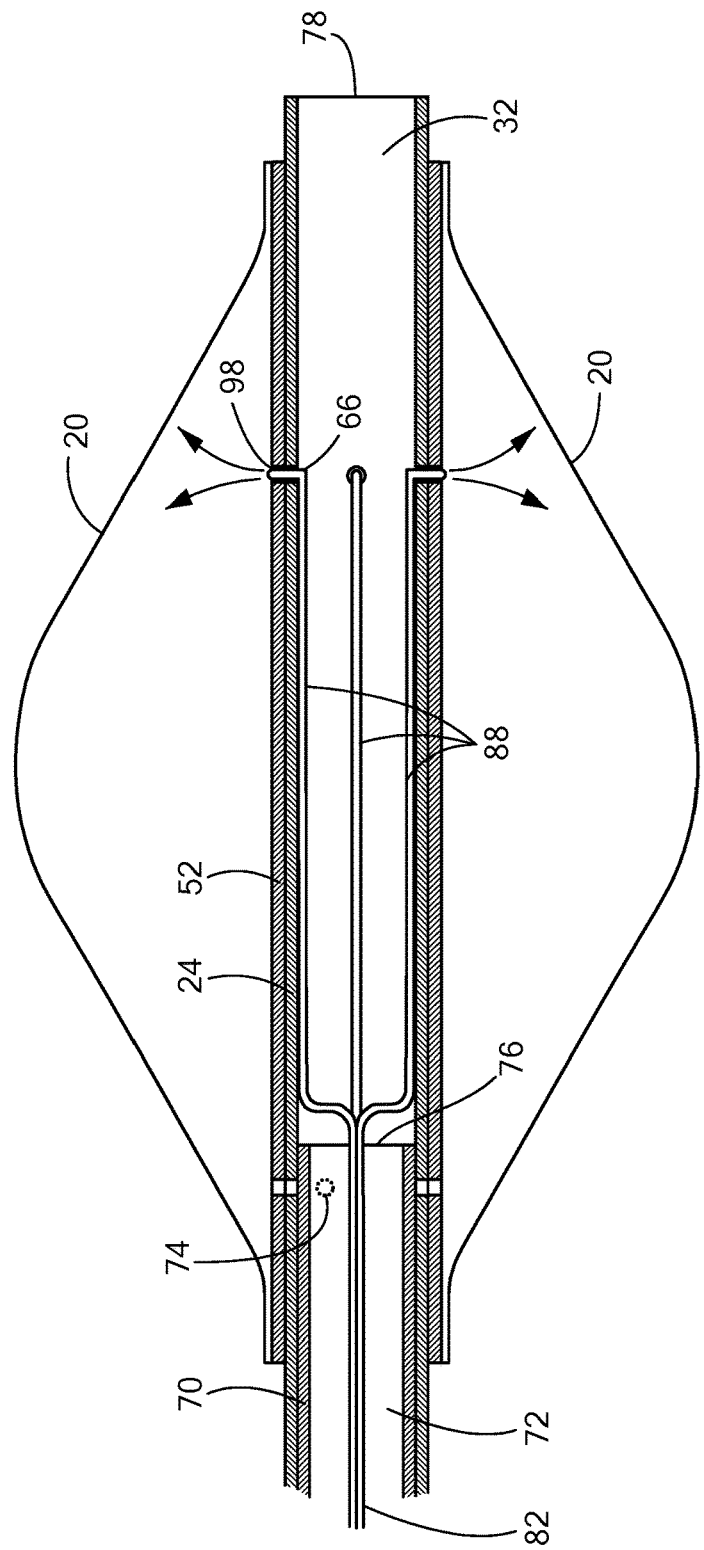
Figure 9D:
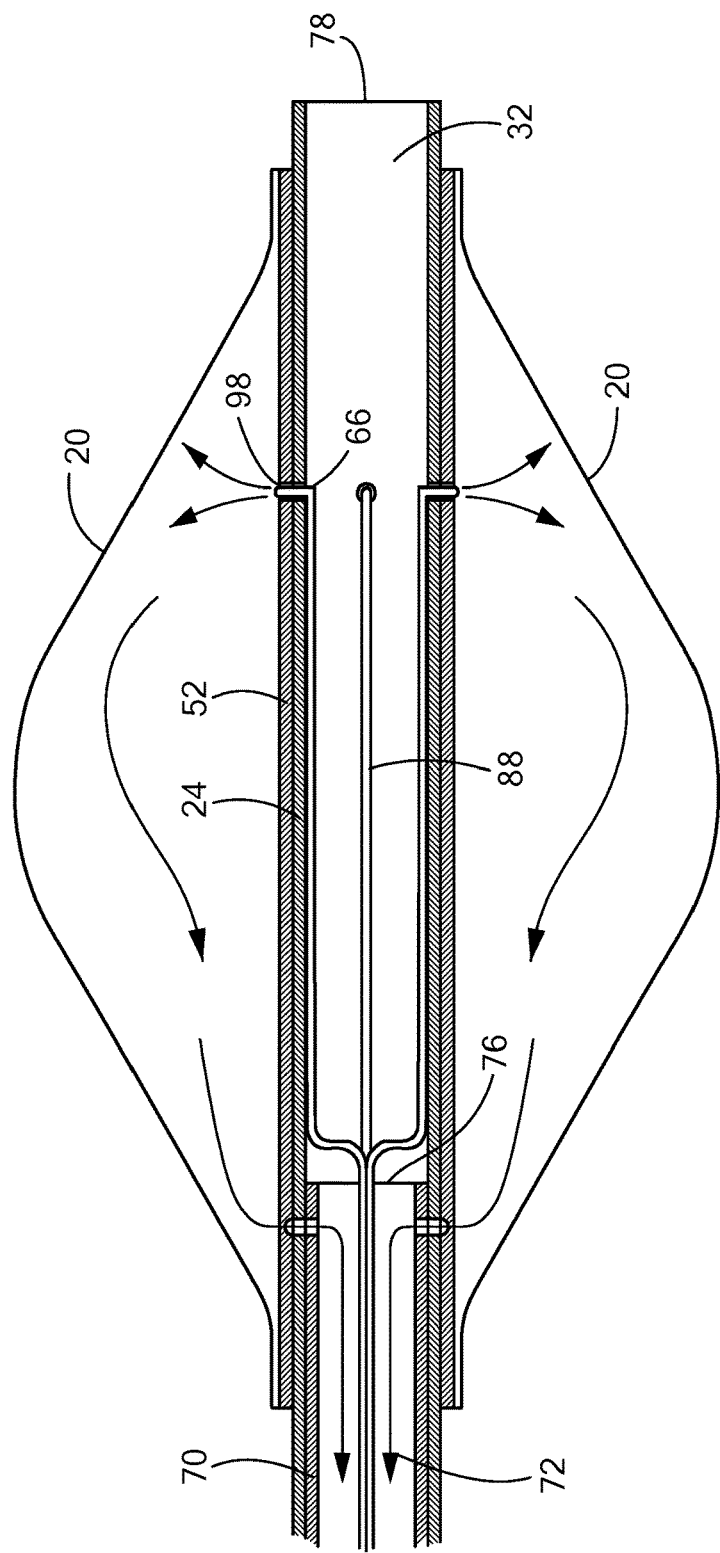

Referring now to FIGS. 9A-9D, configurations of the inner elongate body within the treatment catheter during a cryotreatment procedure are shown. The treatment catheter 12 may first be navigated through the patient's vasculature to a target treatment site. As a non-limiting example, the treatment catheter 12 may be navigated to the left atrium of the patient's heart, to a location at which the balloon treatment element 18 is in contact with or proximate a pulmonary vein ostium. Once the treatment catheter 12 is at the desired location, the balloon lobes 20 may be inflated during a primary inflation cycle. As shown in FIG. 9A, during the primary inflation cycle, the inner elongate body 70 may be positioned such that the inner elongate body apertures 74 are open (that is, such that the inner elongate body apertures 74 are fully aligned with the first apertures 64 of the elongate body 24 and the first apertures 60 of each balloon lobe 20). An inflation fluid may then be delivered from the inflation fluid reservoir 38 through the main lumen 32 of the elongate body 24, from where it passes through the apertures 74 of the inner elongate body 70, the first apertures 64 of the elongate body 24, and the first apertures 60 of the balloon lobes 20. The inflation fluid may continue to be delivered this way until all of the balloon lobes 20 are inflated and the balloon treatment element 18 has an at least approximately circular cross-sectional shape. Any suitable inflation fluid may be used, such as room-temperature nitrous oxide ($N_2O$) vapor. As is shown in FIG. 9B, the inner elongate body 70 may then be rotated either clockwise or counterclockwise such that the inner elongate body apertures 74 are closed (that is, no longer fully aligned with the first apertures 64 of the elongate body 24 and the first apertures 60 of each balloon lobe 20). In this position, fluid flows from the main lumen 32 into the balloon lobes 20, and evacuation of fluid from the balloon lobes 20 into the main lumen 32, may be prevented. Although not shown, the inner elongate body 70 may alternatively be moved longitudinally (advanced or retracted) within the elongate body 24 so the inner elongate body apertures 74 are no longer open or aligned with the first apertures 64 of the elongate body 24 and the balloon lobes 20.

As is shown in FIG. 9C, inflation fluid may be delivered from the inflation fluid reservoir 38 through the delivery lumen 82 and into each of the linear segments 88 at the distal portion of the delivery lumen 82 in a secondary inflation cycle. The inflation fluid may then pass through the delivery apertures 98 of the fluid delivery segments 96 and into the inner chambers 56 of the balloon lobes 20. Due to the closed configuration of the inner elongate body apertures 74, fluid passing into the balloon lobes 20 may continue to inflate, and therefore increase the size of, each of the balloon lobes to which the inflation fluid is delivered. As a non-limiting example, the pulmonary vein may have an asymmetric morphology. In order to ensure contact between the entire or at least substantially the entire circumference of the balloon treatment element 18, one or more balloon lobes may be further inflated using the secondary inflation cycle so that extend farther from the catheter 12 longitudinal axis than other balloon lobes. In other words, the outer surface of the balloon at the widest portion of some balloon lobes may be located at a greater radial distance from the catheter longitudinal axis than others. Thus, these larger balloon lobes may bridge the gap between the balloon treatment element 18 and the wall of the pulmonary vein. Inflation fluid may be delivered to all or fewer than all of the balloon lobes 20 during the secondary inflation cycle.

Once the balloon treatment element 18 has the desired configuration and while the injection has started, the inner elongate body 70 may be rotated clockwise or counterclockwise until the inner elongate body apertures 74 are partially open (that is, such that the inner elongate body apertures 74 are partially aligned with the first apertures 64 of the elongate body 24 and the first apertures 60 of the balloon lobes 20), which defines the transition phase. Then, the elongate body apertures 74 are fully open once the ablation has reached its normal flow and/or pressure. The cryogenic refrigerant may be delivered from a cryogenic refrigerant reservoir 36 through the delivery lumen 82 and into the balloon lobes 20, as the inflation fluid was delivered in the secondary inflation cycle. During this transitional phase between inflation and ablation, cryogenic refrigerant may be injected into the balloon lobes 20 and may gradually replace the inflation fluid, which may be evacuated through the first balloon lobe apertures 60 and into the main lumen 32. Additionally, the main lumen 32 may be in fluid communication with a vacuum source 40, which may facilitate evacuation of inflation fluid and cryogenic refrigerant from the balloon lobes 20. The differential injection pressures between the balloon lobes 20 will maintain the multi-lobe balloon shape during ablation.

If the treatment catheter 12 is navigated to other treatment locations, such as a wall of the left atrium, the balloon lobes that are in contact with the target tissue may be inflated using only the delivery lumen 82 as described above for the secondary inflation cycle. Further, the inner elongate body 70 may be positioned such that the inner elongate body apertures 74 are closed. In this manner, fewer than all of the balloon lobes may be inflated.

Figure 10:
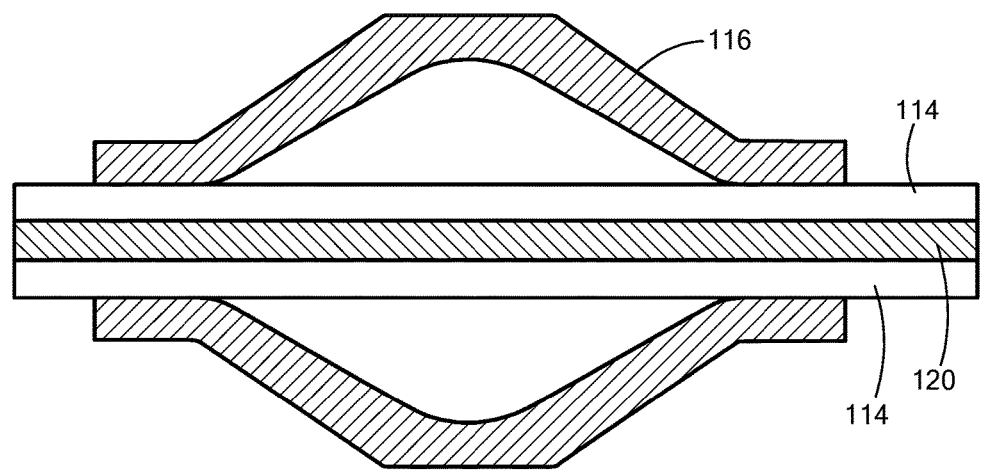
FIGS. 10 and 11 show cross-sectional views of thermoplastic tubes within a mold for forming the multi-lobed balloon treatment element.
Figure 11:
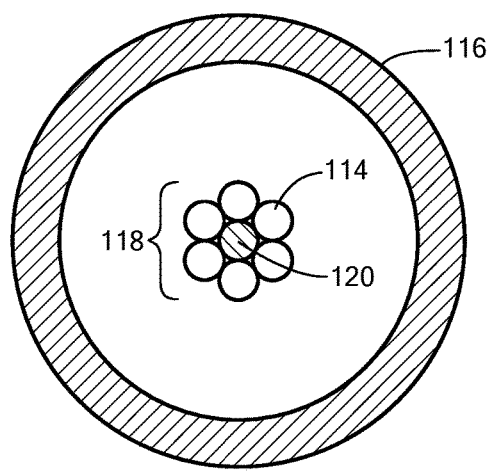

Referring now to FIGS. 10 and 11, a method of manufacturing a multi-lobed balloon treatment element is shown. Specifically, a lateral cross-sectional view of thermoplastic tubes 114 within a mold 116 for forming the multi-lobed balloon treatment element 18 is shown in FIG. 10, and a distal cross-sectional view of the same is shown in FIG. 11. A plurality of extruded thermoplastic tubes 114, one for each balloon lobe, may be initially bonded to each other in a radial array to form a parison 118 around a core 120 (as shown in FIG. 11) using an adhesive, thermal bonding, laser welding, or the like. The parison 118 may be positioned within a mold 116 that is shaped similar to the inflated balloon treatment element 18. Each thermoplastic tube 114 may then be expanded using compressed air/gas to conform to the shape of the mold 116.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A cryotreatment catheter, comprising:
an elongate body including a distal portion with a distal end, a proximal portion, and a lumen therebetween, the distal portion of the elongate body including a first plurality of apertures and a second plurality of apertures located distal to the first plurality of aperture, each of the first plurality of apertures and the second plurality of apertures being radially arranged around the elongate body; and
a balloon treatment element coupled to the distal portion of the elongate body, the balloon treatment element including a plurality of balloon lobes radially arranged around the elongate body, each of the first plurality of apertures and the second plurality of apertures corresponding to one of the plurality of balloon lobes, each of the plurality of balloon lobes including:
an attachment spine affixed to the distal portion of the elongate body;
a tissue contact surface opposite the attachment spine; and
a first lateral surface and a second lateral surface, each of the first lateral surface and the second lateral surface being at least substantially planar, the first lateral surface of each of the plurality of balloon lobes being in contact with the second lateral surface of an adjacent one of the plurality of balloon lobes.

2. The cryotreatment catheter of claim 1, further comprising an outer balloon that surrounds the plurality of balloon lobes.

3. The cryotreatment catheter of claim 1, wherein the tissue contact surface defines a surface area and the attachment spine defines a surface area, the surface area of the tissue contact surface being greater than the surface area of the attachment spine.

4. The cryotreatment catheter of claim 1, wherein each of the plurality of balloon lobes includes:
a first aperture that is radially aligned with one of the first plurality of apertures of the elongate body; and
a second aperture that is radially aligned with one of the second plurality of apertures of the elongate body, the second aperture being located distal to the first aperture.

5. The cryotreatment catheter of claim 4, wherein each of the first aperture and the second aperture are in the attachment spine.

6. The cryotreatment catheter of claim 4, wherein the elongate body is an outer elongate body, the cryotreatment catheter further comprising an inner elongate body including a distal portion, a proximal portion, a lumen therebetween, and a plurality of apertures radially arranged around the inner elongate body.

7. The cryotreatment catheter of claim 6, wherein each of the plurality of apertures of the inner elongate body corresponds to one of the first plurality of apertures of the outer elongate body.

8. The cryotreatment catheter of claim 6, wherein the distal portion of the inner elongate body defines a distal end, the distal end of the inner elongate body being distal to the first plurality of apertures of the outer elongate body.

9. The cryotreatment catheter of claim 4, wherein the cryotreatment catheter further includes a delivery lumen at least partially located within the elongate body.

10. The cryotreatment catheter of claim 9, wherein the delivery lumen includes:
a proximal portion located within the elongate body; and
a branched distal portion located within the elongate body distal to the distal end of the elongate body, the branched distal portion including a plurality of linear segments, each of the plurality of linear segments being in fluid communication with a corresponding one of the plurality of balloon lobes.

11. The cryotreatment catheter of claim 10, wherein each of the linear segments includes a distal tip portion that has a delivery aperture, each of the distal tip portions extending from a corresponding linear segment at an approximately 90° angle, each of the distal tip portions extending through a corresponding one of the second plurality of apertures of the elongate body and a corresponding second aperture of one of the plurality of balloon lobes.

12. A cryotreatment catheter, comprising:
an outer elongate body including a distal portion, a proximal portion, and a lumen extending between the distal portion and the proximal portion, the distal portion defining a distal end;
a balloon treatment element coupled to the distal portion of the outer elongate body, the balloon treatment element including a plurality of balloon lobes radially arranged around the outer elongate body;
an inner elongate body located within and at least one of rotatably and linearly movable within the lumen of the outer elongate body, the inner elongate body including a distal portion, a proximal portion, and a lumen extending between the distal portion and the proximal portion, the distal portion defining a distal end that is located proximal to the distal end of the outer elongate body; and
a fluid delivery lumen located within the lumen of the outer elongate body and at least partially within the lumen of the inner elongate body, the fluid delivery lumen including:
a proximal portion located within the inner elongate body;
a branched distal portion located within the outer elongate body, the branched distal portion including a plurality of linear segments, each of the plurality of linear segments being in fluid communication with a corresponding one of the plurality of balloon lobes; and
a divergence point between the proximal portion and the branched distal portion, the divergence point being distal to the distal end of the inner elongate body.

13. The cryotreatment catheter of claim 12, wherein the outer elongate body includes a first plurality of apertures and a second plurality of apertures located distal to the first plurality of apertures, each of the first plurality of apertures and the second plurality of apertures being radially arranged around the outer elongate body and corresponding to one of the plurality of balloon lobes.

14. The cryotreatment catheter of claim 13, wherein each of the plurality of balloon lobes includes:
an attachment spine coupled to the outer elongate body;
a tissue contact surface opposite the attachment spine; and
a first lateral surface and a second lateral surface, each of the first and second lateral surfaces being at least substantially planar.

15. The cryotreatment catheter of claim 14, wherein the tissue contact surface defines a surface area and the attachment spine defines a surface area, the surface area of the tissue contact surface being greater than the surface area of the attachment spine.

16. The cryotreatment catheter of claim 14, wherein each of the plurality of balloon lobes includes:
a first aperture in the attachment spine that is radially aligned with one of the first plurality of apertures of the elongate body; and
a second aperture in the attachment spine that is radially aligned with one of the second plurality of apertures of the elongate body, the second aperture being located distal to the first aperture.

17. The cryotreatment catheter of claim 16, wherein the inner elongate body includes a plurality of apertures radially arranged around the inner elongate body, each of the apertures of the inner elongate body corresponding to one of the first plurality of apertures of the outer elongate body.

18. The cryotreatment catheter of claim 13, wherein each of the outer elongate body and the inner elongate body include a longitudinal axis, the longitudinal axis of the inner elongate body being coaxial with the longitudinal axis of the outer elongate body, and the inner elongate body is configured to obstruct the first plurality of apertures of the outer elongate body when the inner elongate body is at least one of rotated and linearly moved along its longitudinal axis.

* * * * *